United States Patent
Hestad et al.

(10) Patent No.: US 8,292,925 B2
(45) Date of Patent: Oct. 23, 2012

(54) FLEXIBLE MEMBER WITH VARIABLE FLEXIBILITY FOR PROVIDING DYNAMIC STABILITY TO A SPINE

(75) Inventors: Hugh D. Hestad, Edina, MN (US); Steven L. Griffith, Eden Prairie, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1170 days.

(21) Appl. No.: 11/765,046

(22) Filed: Jun. 19, 2007

(65) Prior Publication Data
US 2008/0319486 A1    Dec. 25, 2008

(51) Int. Cl.
*A61B 17/70*    (2006.01)
(52) U.S. Cl. ....................................... 606/255
(58) Field of Classification Search ........... 606/254–259
See application file for complete search history.

(56) References Cited

U.S. PATENT DOCUMENTS

| | | | |
|---|---|---|---|
| 4,743,260 A | 5/1988 | Burton | |
| 5,192,327 A * | 3/1993 | Brantigan | 623/17.11 |
| 5,375,823 A | 12/1994 | Navas | |
| 5,540,688 A | 7/1996 | Navas | |
| 5,562,660 A | 10/1996 | Grob | |
| 6,102,912 A * | 8/2000 | Cazin et al. | 606/86 A |
| 6,290,700 B1 | 9/2001 | Schmotzer | |
| 6,986,771 B2 | 1/2006 | Paul et al. | |
| 7,828,825 B2 * | 11/2010 | Bruneau et al. | 606/260 |
| 2002/0035366 A1 | 3/2002 | Walder et al. | |
| 2004/0049002 A1 | 3/2004 | Andrews et al. | |
| 2004/0049189 A1 | 3/2004 | Le Couedic et al. | |
| 2004/0215191 A1 * | 10/2004 | Kitchen | 606/61 |
| 2005/0056979 A1 | 3/2005 | Struder et al. | |
| 2005/0065514 A1 | 3/2005 | Struder | |
| 2005/0096652 A1 | 5/2005 | Burton | |
| 2005/0203513 A1 | 9/2005 | Jahng et al. | |
| 2005/0277922 A1 * | 12/2005 | Trieu et al. | 606/61 |
| 2006/0066685 A1 | 3/2006 | Sugahara | |
| 2006/0111715 A1 | 5/2006 | Jackson | |
| 2006/0142758 A1 | 6/2006 | Petit | |
| 2006/0167550 A1 | 7/2006 | Snell et al. | |
| 2006/0247638 A1 | 11/2006 | Trieu et al. | |
| 2007/0016200 A1 | 1/2007 | Jackson | |

(Continued)

FOREIGN PATENT DOCUMENTS

DE    10 2004 048 939 A1    5/2005

(Continued)

OTHER PUBLICATIONS

U.S. Appl. No. 11/618,943 to Hestad et al. titled "Spine Stiffening Device", filed Jan. 2, 2007.

*Primary Examiner* — Eduardo C Robert
*Assistant Examiner* — Jerry Cumberledge
(74) *Attorney, Agent, or Firm* — Seager Tufte & Wickhem LLC

(57) ABSTRACT

The present invention relates to spinal support devices and, more specifically, to a flexible member having variable flexibility for use with a dynamic stabilization system or implant to provide dynamic stability to a person's spine. The flexible member generally includes a first material having a first portion including a first material having a first elasticity and a second portion including a second material having a second elasticity greater than the first to provide the flexible member with a variable flexibility.

12 Claims, 5 Drawing Sheets

U.S. PATENT DOCUMENTS

| | | | |
|---|---|---|---|
| 2007/0049937 A1* | 3/2007 | Matthis et al. | 606/61 |
| 2007/0055244 A1 | 3/2007 | Jackson | |
| 2007/0093814 A1* | 4/2007 | Callahan et al. | 606/61 |
| 2007/0100341 A1 | 5/2007 | Reglos et al. | |
| 2007/0129729 A1 | 6/2007 | Petit et al. | |
| 2007/0178005 A1* | 8/2007 | Broadley et al. | 419/37 |
| 2007/0191841 A1* | 8/2007 | Justis et al. | 606/61 |
| 2007/0233064 A1* | 10/2007 | Holt | 606/61 |
| 2007/0233073 A1* | 10/2007 | Wisnewski et al. | 606/61 |
| 2007/0233095 A1 | 10/2007 | Schlaepfer | |
| 2007/0270821 A1 | 11/2007 | Trieu et al. | |
| 2007/0270860 A1 | 11/2007 | Jackson | |
| 2007/0293862 A1 | 12/2007 | Jackson | |
| 2008/0091213 A1 | 4/2008 | Jackson | |
| 2008/0140076 A1 | 6/2008 | Jackson | |
| 2008/0147122 A1 | 6/2008 | Jackson | |
| 2008/0172091 A1* | 7/2008 | Anderson | 606/246 |
| 2008/0177317 A1 | 7/2008 | Jackson | |
| 2008/0183213 A1* | 7/2008 | Veldman et al. | 606/257 |
| 2008/0183216 A1 | 7/2008 | Jackson | |
| 2008/0300633 A1* | 12/2008 | Jackson | 606/257 |
| 2009/0005817 A1 | 1/2009 | Friedrich et al. | |
| 2009/0093844 A1* | 4/2009 | Jackson | 606/254 |

FOREIGN PATENT DOCUMENTS

| | | |
|---|---|---|
| EP | 0 516 567 A1 | 12/1992 |
| EP | 0669109 | 8/1995 |
| FR | 2 844 180 A1 | 3/2004 |
| WO | WO9417745 | 8/1994 |
| WO | WO0211975 A1 | 2/2002 |
| WO | WO2007127604 A2 | 8/2007 |
| WO | 2008134703 A2 | 11/2008 |

* cited by examiner

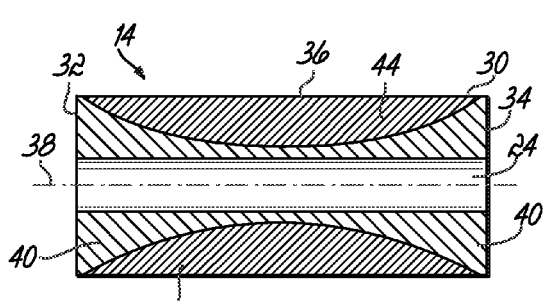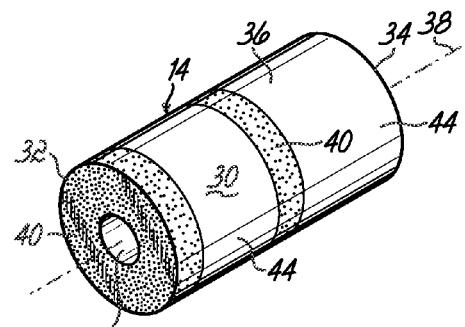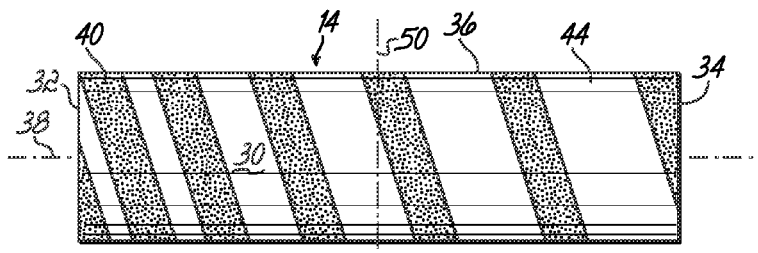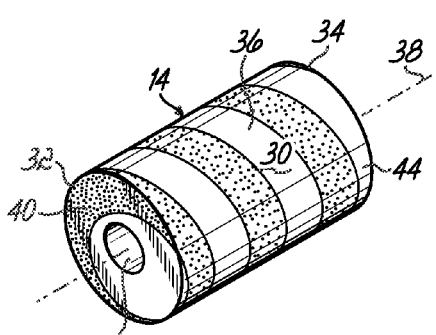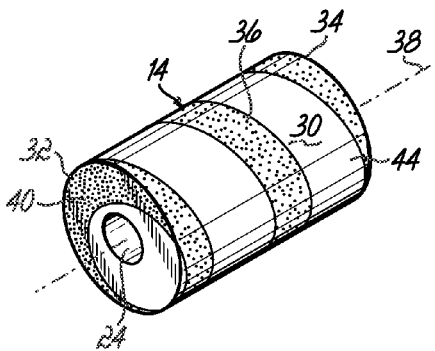

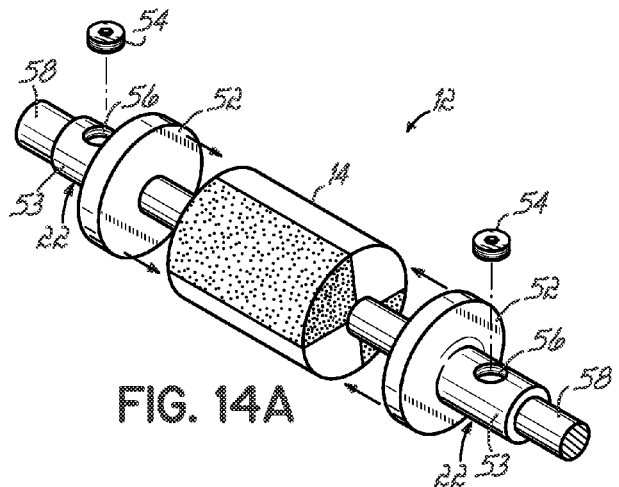
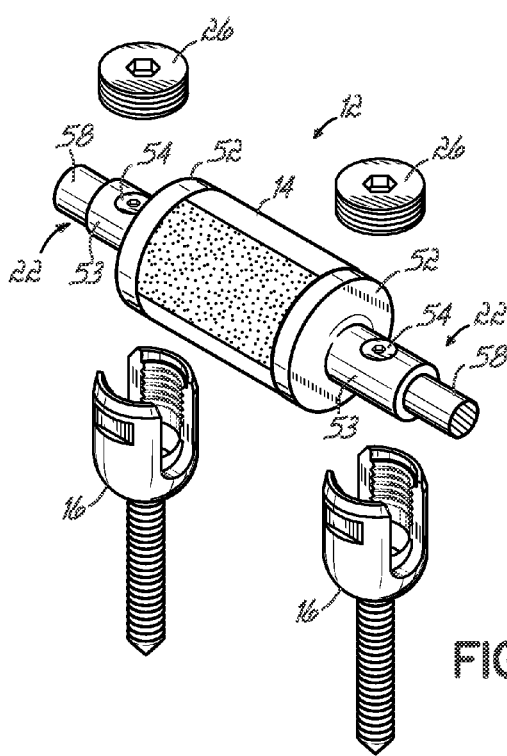
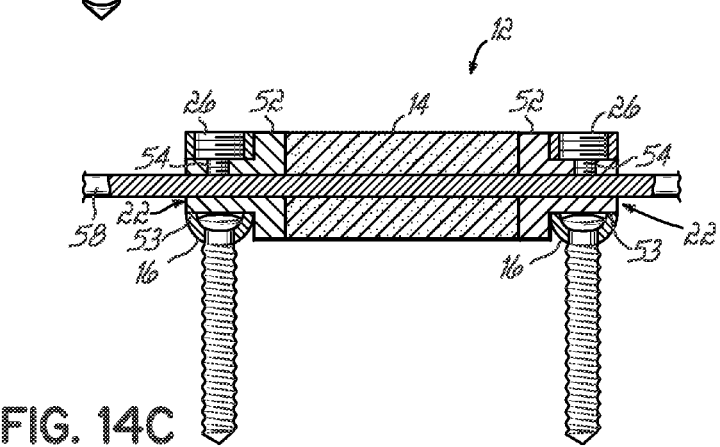
FIG. 14A
FIG. 14B
FIG. 14C

FLEXIBLE MEMBER WITH VARIABLE FLEXIBILITY FOR PROVIDING DYNAMIC STABILITY TO A SPINE

FIELD OF THE INVENTION

The present invention relates generally to spinal support devices and, more specifically, to a flexible member having variable flexibility for use with a dynamic stabilization system to provide dynamic stability to a person's spine.

BACKGROUND OF THE INVENTION

The treatment of acute and chronic spinal instabilities or deformities of the thoracic, lumbar, and sacral spine has traditionally involved the implantation of rigid rods to secure the vertebrae of a patient. More recently, flexible materials have been utilized in connection with anchor members, e.g., pedicle screws, to provide a dynamic stabilization of the spinal column. Such dynamic stabilization systems or implants typically include a flexible member positioned between pedicle screws installed in adjacent vertebrae of a person's spine.

Certain dynamic stabilization systems permit the top loading of a flexible member and connecting member between pedicle screws. One such top loading system is disclosed in U.S. Patent Application Publication No. 2002/0035366 to Walder et al., titled "Pedicle Screw For Intervertebral Support Elements", which is expressly incorporated by reference herein in its entirety. Another top loading system is disclosed in U.S. patent application Ser. No. 11/618,943 to Hestad et al., titled "Spine Stiffening Device", which is expressly incorporated by reference herein in its entirety. Still other dynamic stabilization systems are adapted to securely retain the flexible member between pedicle screws without the use of a connecting member.

While current dynamic stabilization systems include flexible members, these flexible members are known to be composed, for example, of a specific material having a singular elasticity that does not allow for variability in flexibility, except by varying the length of the flexible member between pedicle screws. In other words, those flexible members provide an equal bending force in all directions, i.e., the flexible member is without variable flexibility. Such variability in flexibility could provide surgeons with greater options in selecting the most appropriate flexible member for placement at a specific location along a patient's spine, such selection being dictated by the desired bending movement of the flexible member at that location.

Accordingly, it would be desirable to provide flexible members having variable flexibility for use with dynamic stabilization systems to provide dynamic stability to a person's spine that addresses these and other deficiencies of current flexible members.

SUMMARY OF THE INVENTION

In the present invention, a flexible member is provided having variable flexibility for use with a dynamic stabilization system or implant to provide dynamic stability to a person's spine. To that end, the flexible member generally includes a body having opposing first and second ends connected by an intermediate portion extending therebetween. Each opposing end is configured for cooperation with an anchor member, such as a pedicle screw. The body further includes at least one first portion including a first material having a first elasticity and at least one second portion including a second material having a second elasticity greater than the first to provide the flexible member with a variable flexibility. The body can further define a cylinder and may include an aperture extending lengthwise therethrough for receiving a connecting member to retain the flexible member between pedicle screws in the dynamic stabilization system.

In one embodiment, the first material is a different material than the second material. In one example, the first portion of the flexible member includes a plurality of first portions including a first material and the second portion includes a plurality of second portions including a second material. The body further includes a lengthwise central axis, with the plurality of first and second portions extending along the length of the body and being alternately situated, e.g., symmetrically, about the axis thereof. In another example, the plurality of first and second portions are alternately situated circumferentially about the lengthwise central axis along the length of the body. In yet another example, the first portion spirals along the length of the body with a remainder of the body including the second portion.

In another embodiment, the first and second materials are the same type of polymer, with the first and second materials having a predetermined stoichiometry and thermal history, thereby providing the first and second elasticity, respectively, for the first and second portions. In one example, the body defines a flexibility gradient that extends along the length thereof. The flexibility gradient can increase in flexibility from the first end to the opposing second end to define a plurality of elasticities, which includes the first and second elasticity for the first and second portions.

Accordingly, these and other various configurations of the flexible member can allow for easier bending of the flexible member in one direction relative to another, as compared to conventional flexible members which have equal bending force in all directions.

By virtue of the foregoing, there is provided a flexible member having variable flexibility for use with a dynamic stabilization system to provide dynamic stability to a person's spine.

The features and objectives of the present invention will become more readily apparent from the following Detailed Description taken in conjunction with the accompanying drawings.

BRIEF DESCRIPTION OF THE DRAWING

The accompanying drawings, which are incorporated in and constitute a part of this specification, illustrate an embodiment of the invention and, together with the general description of the invention given above, and detailed description given below, serve to explain the invention.

FIG. 7 is a cross-sectional view of the flexible member of FIG. 6 taken along the line 7-7;

FIG. 8 is a perspective view of another embodiment of a flexible member;

FIG. 9 is a side elevational view of another embodiment of a flexible member;

FIGS. 9A and 9B are perspective views of respective left and right sections of the flexible member of FIG. 9 taken along the cut line;

FIG. 14A is a disassembled, perspective view of an embodiment of a connecting member with the flexible member of FIG. 1B for use in a dynamic stabilization system;

FIG. 14B is a partially disassembled view of a dynamic stabilization system utilizing the connecting member and flexible member shown in FIG. 14A and top loading anchor members; and FIG. 14C is a cross-sectional view of the assembled dynamic stabilization system of FIG. 14B.

DETAILED DESCRIPTION OF THE INVENTION

Figure 1A:
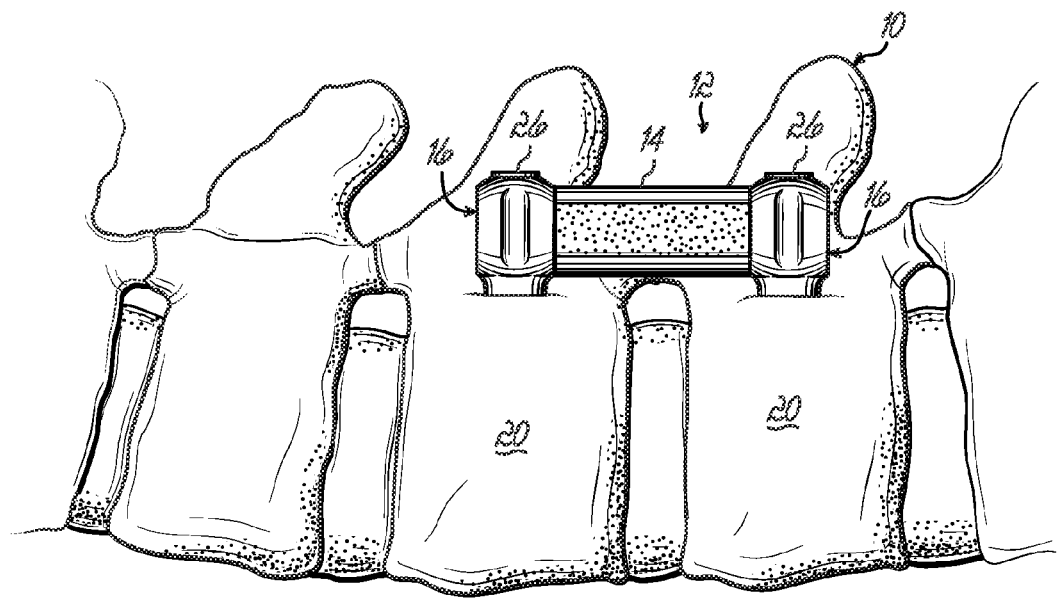
FIG. 1A is a side elevational view of a dynamic stabilization system including anchor members inserted into the spinal column and a flexible member secured therebetween.
Figure 1B:
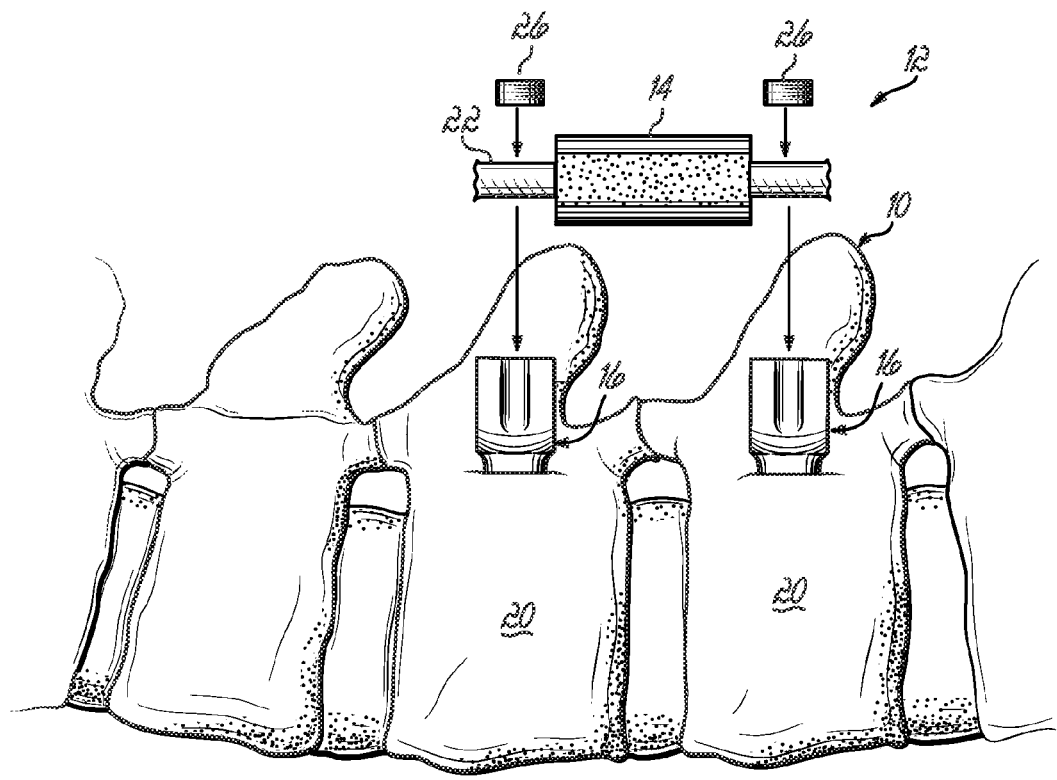
FIG. 1B is a side elevational view of a dynamic stabilization system including top loading anchor members inserted into the spinal column and a flexible member with connecting member being secured therebetween.

FIGS. 1A and 1B illustrate cut-away sections of a spine 10 having a dynamic stabilization system or implant 12 implanted therein. The systems 12 of FIGS. 1A and 1B, include a flexible member 14 having variable flexibility positioned between anchor members 16, for example, pedicle screws, installed in adjacent vertebrae 20 of the spine 10.

The anchor members 16 of FIGS. 1A and 1B generally illustrate top loading pedicle screws that retain the flexible members 14 therebetween by means well known in the art. One such top loading type screw is disclosed in U.S. Patent Application Publication No. 2002/0035366 to Walder et al., titled "Pedicle Screw For Intervertebral Support Elements", which is expressly incorporated by reference herein in its entirety. With further reference to FIG. 1B, a connecting member 22 may be passed through an aperture 24 (FIG. 2B) in the flexible member 14, such connecting member 22 then being top loaded and secured within a top portion of each anchor member 16 by threadable cap members 26. The connecting member 22 can be passed through the aperture 24 during or prior to implantation in a patient, or preformed or coupled to the flexible member 14 to form a unitary structure during manufacture of the dynamic stabilization system 12. Once secured, that connecting member 22 retains the flexible member 14 between the anchor members 16 while cooperating with the flexible member 14 for permitting mobility of the spine 10. In contrast, the flexible member 14 of FIG. 1A is devoid of aperture 24 and corresponding connecting member 22 and, instead, is directly top loaded into anchor members 16 and securely held in place by threadable cap members 26.

Figure 2A:
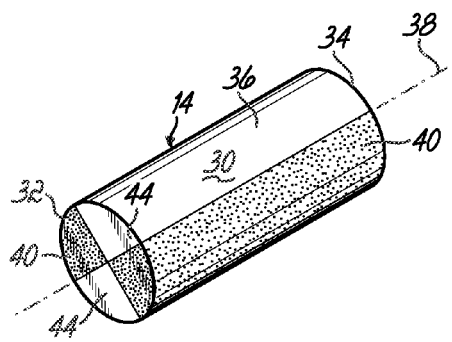
FIG. 2A is a perspective view of the flexible member of FIG. 1A.
Figure 2B:
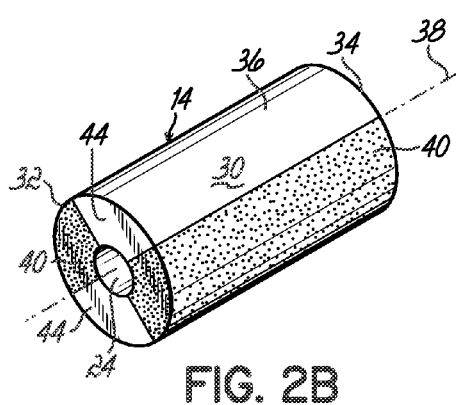
FIG. 2B is a perspective view of the flexible member of FIG. 1B.

In accordance with embodiments of the present invention, the flexible members 14 of FIGS. 1A and 1B, as best shown in FIGS. 2A and 2B, respectively, include a cylindrical body 30 including opposing first and second ends 32 and 34 connected by an intermediate portion 36 extending therebetween. In this embodiment, each opposing end 32, 34 is configured for cooperation with a corresponding anchor member 16. The body 30 further includes a lengthwise central axis 38 and a plurality of first portions 40, i.e., two first portions, including a first material, for example, a first polymeric material, having a first elasticity and a plurality of second portions 44, i.e., two second portions, including a second material, for example, a second polymeric material, having a second elasticity greater than the first to provide the flexible member 14 with a variable flexibility. The first material may be a different material than the second material. In addition, the plurality of first portions 40 as well as the plurality of second portions 44 may have different elasticities and/or may be composed of different material, including, for example, polymeric, metal, or ceramic materials having a range of elasticities from flexible, to rigid, to semi-rigid that result in a flexible member that can be tailored to a particular surgical application.

Additionally, the first and second portions 40, 44 extend along the length of the body 30 and are alternately spaced symmetrically about the axis 38 of the body 30. Although not shown, the first and second portions 40, 44 could be spaced asymmetrically about the axis 38. The flexible member of FIG. 2B further includes aperture 24 extending lengthwise through the body 30 for receiving the connecting member 22.

While two first and two second portions 40, 44 are illustrated in FIGS. 2A and 2B, in its simplest form one first portion 40 and one second portion 44 can be provided. In addition, the width of the portions 40, 44 may be varied. And, despite the absence of a connecting member 22 in the system 12 of FIG. 1A, it should be understood by one of ordinary skill in the art that the flexible member 14 of FIG. 2B could be used in the system 12 of FIG. 1A. The flexible member 14 also may be provided in varying lengths, e.g., twelve-inch lengths, so that a surgeon can cut, or shape, the flexible member 14 to fit between opposing anchor members 16 along a specific section of spine 10 as well as to accommodate a desired bending movement of the flexible member 14. The construction of flexible member 14 shown in FIGS. 2A and 2B provides a cross-sectional flexibility gradient that is dependent upon the elastomeric characteristics of the first and second portions 40, 44.

Orientation of the flexible member 14, e.g., inferior or superior positioning of one end 32, 34 relative to the spine 10 and/or lateral versus anterior/posterior positioning of the first and second portions 40, 44, is determined by the desired bending movement of the selected flexible member 14 at that specific section of spine 10. In other words, orientation of the flexible member 14 is generally determined based upon the needs of the patient, with the flexible member 14 of the present invention allowing for tailoring thereof on a patient-by-patient basis. In addition, although the flexible member 14 is illustrated as being cylindrical, it should be understood by one having ordinary skill in the art that other desired shapes, for example, square, rectangular, oval, etc. may be utilized.

With respect to the bending movement of the flexible member 14, if the first material of the flexible member 14 is located anterior/posterior (A-P) relative to the spine 10 and the second material is located laterally, the flexible member 14 can allow for easier bending A-P as compared to laterally. Consequently, the flexible member 14 could be rotated 90 degrees and then the A-P bending would require more force to allow similar ease of bending in contrast to lateral bending. The surgeon implanting the dynamic stabilization system 12 can selectively take advantage of the varying elasticity of the portions 40, 44 of flexible member 14 to treat an indication or condition in the patient. The surgeon can be provided with a plurality of pre-constructed systems 12 that have flexible members with varying flexibility characteristics, or, alternatively, be provided with a variety of flexible members with varying flexibility characteristics any one of which can be incorporated into a system 12 that is constructed during the surgical procedure.

Figure 3:
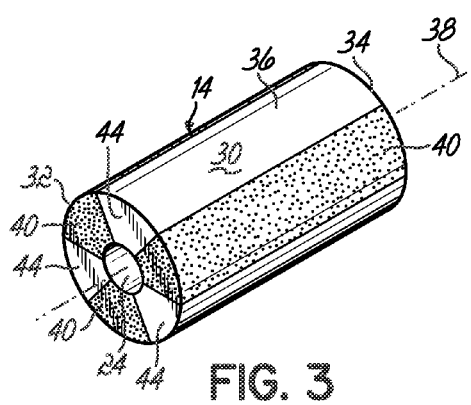
FIGS. 3-6 are perspective views of various embodiments of a flexible member.

FIG. 3 depicts another embodiment of flexible member 14, which is similar to FIG. 2B. The flexible member 14 of FIG. 3 similarly includes the plurality of first portions 40 including a first material having a first elasticity and the plurality of second portions 44 including a second material having a second elasticity greater than the first to provide the flexible member 14 with variable flexibility. However, rather than two first portions 40 and two second portions 44 as in FIG. 2B, the flexible member 14 of FIG. 3 includes three first portions 40 and three second portions 44. The flexible member 14 further includes aperture 24 extending lengthwise through the body 30 for receiving connecting member 22. It should be understood that the aperture 24 may be eliminated. The construction of flexible member 14 shown in FIG. 3 provides a cross-sectional flexibility gradient that is dependent upon the elastomeric characteristics of the first and second portions 40, 44.

Figure 4:
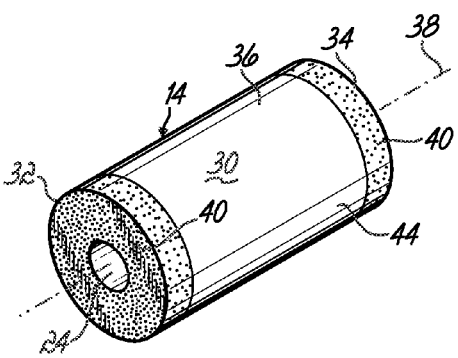

FIG. 4 depicts another embodiment of flexible member 14, which includes the cylindrical body 30 including opposing first and second ends 32, 34 connected by the intermediate portion 36 extending therebetween. The body 30 includes one each of two first portions 40 defining the first and second ends 32, 34, respectively, and a second portion 44 defining the intermediate portion 36. The first portions include a first material having a first elasticity and the second portion 44 includes a second material having a second elasticity greater than the first to provide the flexible member 14 with variable flexibility. The flexible member 14 further includes optional aperture 24 extending lengthwise through the body 30 for receiving connecting member 22. The material and/or elasticity thereof for the first portions 40 may be the same or different. Alternatively, one each of two second portions 44 may define the first and second ends 32, 34, respectively, and a first portion 40 may define the intermediate portion 36. This configuration may allow the ends 32, 34 of the flexible member 14 to desirably conform to the anchor members 16. The construction of flexible member 14 shown in FIG. 4 provides a cross-sectional flexibility gradient that is dependent upon the elastomeric characteristics of the first and second portions 40, 44.

Figure 5:
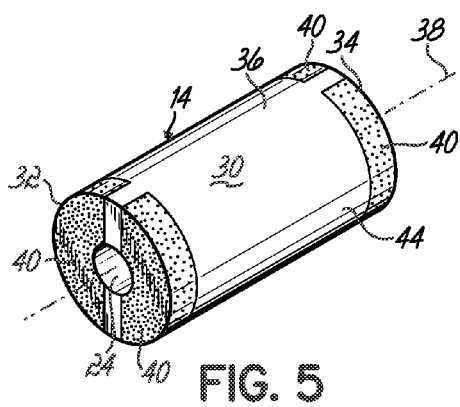

FIG. 5 depicts another embodiment of flexible member 14, which is similar to FIG. 4. Rather than two first portions 40 defining first and second ends 32, 34, respectively, two each of four first portions 40 substantially define the first and second ends 32, 34, respectively. To that end, each of the two first portions 40 of the first and second ends 32, 34 of FIG. 5 define opposing substantially semicircular portions, which together are situated only substantially circumferentially about the lengthwise central axis 38.

Figure 6:
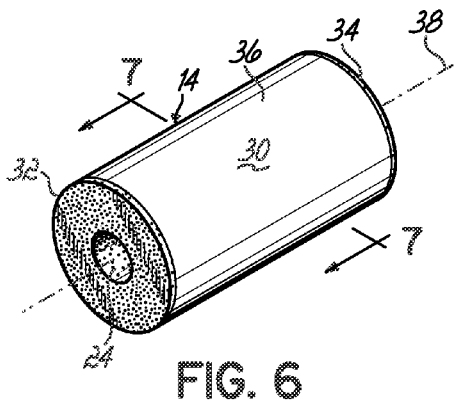

FIGS. 6 and 7 depict another embodiment of flexible member 14, which is also similar to FIG. 4. Specifically, as best shown in FIG. 7, the first portion 40 defines a half-pipe shape that extends along the length of central axis 38. The second portion overlays the half-pipe shape and generally defines a hemispherical shape, whereby the first portion 40 substantially defines the first and second ends 32, 34 and the second portion 44 substantially defines the intermediate portion 36. Thus, the first and second ends 32, 34 substantially include a first material having a first elasticity and the intermediate portion 36 substantially includes a second material having a second elasticity greater than the first to provide the flexible member 14 with variable flexibility. In an alternate embodiment, the second portion 44 defines the half-pipe shape and the first portion 40 overlays the half-pipe shape and generally defines the hemispherical shape. The flexible member 14 further includes optional aperture 24 extending lengthwise through the body 30 for receiving the connecting member 22.

FIG. 8 depicts another embodiment of flexible member 14, which includes cylindrical body 30 including opposing first and second ends 32, 34 connected by intermediate portion 36 extending therebetween. The body 30 further includes lengthwise central axis 38 and a plurality of first portions 40, i.e., two first portions, including a first material having a first elasticity and a plurality of second portions 44, i.e., two second portions, including a second material having a second elasticity greater than the first to provide the flexible member 14 with variable flexibility. The first and second portions 40, 44 are alternately situated circumferentially about the lengthwise central axis 38 along the length of the body 30. The flexible member 14 further includes optional aperture 24 extending lengthwise through the body 30 for receiving connecting member 22. As shown, first end 32 is less flexible than second end 34, and the intermediate portion 36 has alternating regions of flexibility. In an alternate embodiment, the first and second portions 40, 44 may be switched such as to provide a variation in flexibility.

FIG. 9 depicts another embodiment of flexible member 14, which includes cylindrical body 30 including opposing first and second ends 32, 34 connected by intermediate portion 36 extending therebetween. The body 30 further includes lengthwise central axis 38 and first portion 40 including a first material having a first elasticity and second portion 44 including a second material having a second elasticity greater than the first to provide the flexible member 14 with variable flexibility. The first portion 40 spirals along the length of the body 30 with a remainder of the body 30 including the second portion 44. As the spiral extends towards second end 34, the spacing between the turns of the spiral increases to provide the flexible member 14 generally with a cross-sectional and lengthwise flexibility gradient. Other spiral variations may be provided. The flexible member 14 further includes optional aperture 24 extending lengthwise through the body 30 for receiving the connecting member 22.

As with each flexible member 14, the flexible member 14 of FIG. 9 may be provided in varying lengths, e.g., twelve-inch lengths, so that a surgeon can cut, or shape, the flexible member 14 to fit between opposing anchor members 16 along a specific section of spine 10 as well as to accommodate a desired bending movement of the flexible member 14. To that end, during surgery, a surgeon may cut flexible member 14 of FIG. 9, such as along line 50, to provide the flexible members 14 of FIGS. 9A and 9B, respectively, which have different bending properties due to the spacing of the spiral, such spacing providing variable flexibility. The spiral configuration of the flexible members 14 of FIGS. 9, 9A, and 9B can allow for more consistent bending forces in all directions and can provide a desirable spring-action effect.

Figure 10:
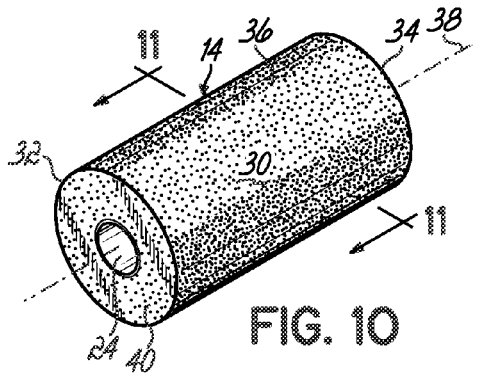
FIG. 10 is a perspective view of another embodiment of a flexible member.
Figure 11:
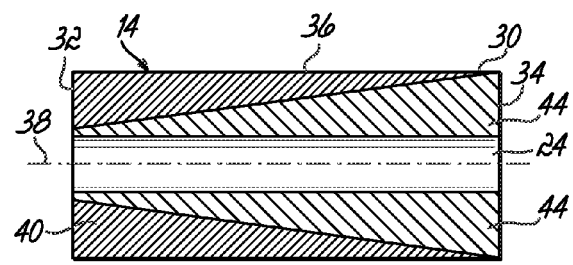
FIG. 11 is a cross-sectional view of the flexible member of FIG. 10 taken along the line 11-11.

FIGS. 10 and 11 depict yet another embodiment of flexible member 14, which includes cylindrical body 30 including opposing first and second ends 32, 34 connected by intermediate portion 36 extending therebetween. The body 30 further includes lengthwise central axis 38 and first portion 40 including a first material having a first elasticity and second portion 44 including a second material having a second elasticity greater than the first to provide the flexible member 14 with variable flexibility. As best shown in FIG. 11, each of the first and second portions 40, 44 are generally triangular-shaped with each base situated at opposing ends 32, 34, respectively, such that first portion 40 substantially defines the first end 32 and second portion 44 substantially defines the second end 34. In other words, the first end 32 substantially includes the first material and the second end 34 substantially includes the second material. The flexible member 14 further includes optional aperture 24 extending lengthwise through the body 30 for receiving the connecting member 22. This configuration provides one end 32 that is less flexible than the other end 34.

The above-described flexible members 14 can be manufactured using injection molding processes as are known in the art. To that end, the proposed configurations may be injection molded using, for example, a one-step process or a multi-step process involving the materials of the flexible member 14. In addition, the desired flexible member 14 also may be extruded using a conventional thermoplastic extrusion process. Such process utilizes multiple extrusion heads having a die nozzle configuration to feed the materials into an extrusion die to form a well-fused combination of materials, i.e., to form the flexible member 14. The flexible member 14 in FIGS. 10 and 11 has a cross-sectional and lengthwise flexibility gradient.

Figure 12:
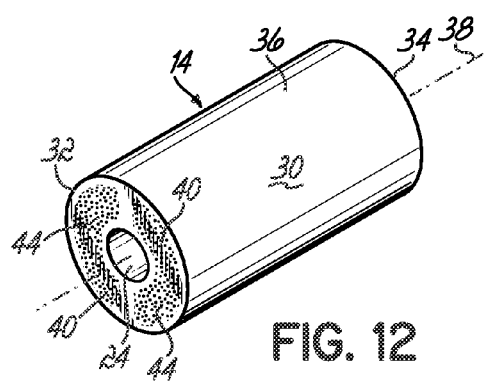
FIG. 12 is a perspective view of another embodiment of a flexible member.

FIG. 12 further depicts still another embodiment of flexible member 14, which is similar to FIG. 2B. However, the first and second materials of FIG. 12 include the same type of polymer, e.g., polyurethane, wherein the first and second materials have a predetermined stoichiometry and thermal history, thereby providing the first and second elasticities, respectively, for the first and second portions. Such flexible member with its material may be formed using the precision polyurethane manufacture method and apparatus disclosed in U.S. Patent Application Publication No. 2004/0049002 to Andrews et al., titled "Precision Polyurethane Manufacture", which is expressly incorporated by reference herein in its entirety.

In the precision polyurethane manufacture process, a polyurethane having a predetermined stoichiometry and thermal history is generally formed by reacting a multifunctional isocyanate, a polyol and, optionally, a chain extender. At least two reagents selected from the isocyanate, the polyol, the chain extender, any mixture thereof and any pre-polymer formed therefrom are intensively mixed prior to being reactively extruded to form the polyurethane. The process is understood to allow control of reagent stoichiometry, while intimate mixing of the reagents at the molecular level allows the manufacture of tailored linear polyurethanes of narrow molecular weight distribution or narrow polydispersity. Moreover, a known and reproducible thermal history can be imparted to the polymer during synthesis, while overall thermal degradation can be minimized by reducing the number of melt cycles for polyurethane components. Such a process allows the integrated manufacture of a polyurethane resin, finished product or aqueous dispersion, while perturbations of the reaction stoichiometry allows the manufacture of polyurethanes with controlled composition and mass distributions.

With reference again to FIG. 12, the flexible member 14 includes cylindrical body 30 including opposing first and second ends 32, 34 connected by intermediate portion 36 extending therebetween. The body 30 further includes lengthwise central axis 38 and a plurality of first portions 40, i.e., two first portions, including a first material having a first elasticity and a plurality of second portions 44, i.e., two second portions, including a second material having a second elasticity greater than the first to provide the flexible member 14 with a variable flexibility. The first and second portions 40, 44 extend along the length of the body 30 and are alternately spaced symmetrically about the axis 38 of the body 30. Again, the first and second materials include the same type of polymer, e.g., polyurethane formed by the precision polyurethane manufacture method discussed above, wherein the material has a predetermined stoichiometry and thermal history thereby providing the first and second elasticities, respectively, for the first and second portions 40, 44. The flexible member 14 further includes optional aperture 24 extending lengthwise through the body 30 for receiving the connecting member 22.

Figure 13:
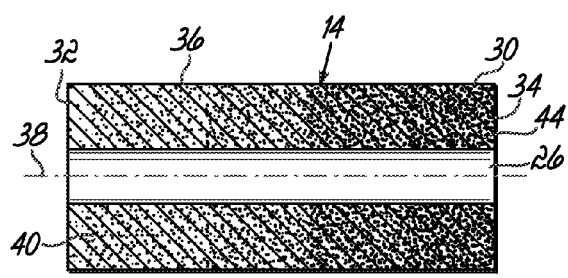
FIG. 13 is a cross-sectional view of another embodiment of a flexible member similar to the flexible member of FIG. 12.

FIG. 13 depicts another embodiment of the flexible member 14, which is similar to FIG. 12 insofar as the first and second materials of the flexible member 14 include the same type of polymer, e.g., polyurethane, wherein the first and second materials having a predetermined stoichiometry and thermal history, thereby providing the first and second elasticities, respectively, for the first and second portions 40, 44. Such flexible member 14 with its material may be formed using the precision polyurethane manufacture method and apparatus as discussed above.

To that end, the flexible member 14 of FIG. 13 includes cylindrical body 30 including opposing first and second ends 32, 34 connected by intermediate portion 36 extending therebetween. The body 30 further includes lengthwise central axis 38 and first portion 40 including a first material having a first elasticity and second portion 44 including a second material having a second elasticity greater than the first to provide the flexible member 14 with a variable flexibility. More specifically, the body 30 of flexible member 14 of FIG. 13 defines a flexibility gradient that extends along the length thereof. The flexibility gradient increases in flexibility from the first end 32 to the opposing second end 34 to define a plurality of elasticities, which includes the first and second elasticity for the first and second portions 40, 44, respectively. The first and second ends 32, 34 substantially define first and second portions 40, 44, which include first and second material respectively. That material has a predetermined stoichiometry and thermal history thereby providing the first and second elasticities, respectively, for the first and second portions 40, 44. In an alternate embodiment, the body 30 can define a flexibility gradient that extends radially outward from the lengthwise central axis 38. Such flexibility gradient can increase or decrease in flexibility in a direction radially outwardly from and circumferentially about the lengthwise central axis. Other variations are contemplated and understood by one having ordinary skill in the art. The flexible member 14 further includes optional aperture 24 extending lengthwise through the body 30 for receiving the connecting member 22.

Accordingly, there is provided flexible member 14 having variable flexibility for use with a dynamic stabilization system 12 to provide dynamic stability to a person's spine 10. Such variability in flexibility, for example, can provide surgeons with greater options in selecting the most appropriate flexible member 14 for placement at a specific location along the spine 10, such selection being dictated by the desired bending movement of the flexible member 14 at that location.

The materials that are used in the flexible members 14 of the present invention may be selected from any suitable biocompatible material as known in the art. By way of example, the materials can include rigid or flexible metals, ceramic materials, carbon fiber, polymeric materials, and/or composite materials. The metals can include titanium or nickel-titanium alloy (NiTiNOL) wire, such as superelastic or shape memory NiTiNOL, for example. The polymeric materials can include, for example, hydrogels (e.g., polyacrylamides), silicone elastomers (natural or synthetic), epoxies (e.g., polyamide epoxy), urethanes, and thermoplastic materials, such as polyurethane, polyethylene (e.g., UHMWPE), polyethylene terephthalate (e.g., Sulene®), polypropylene, polyamide (e.g., Nylon), polyester, acetal, polycarbonate, thermoplastic elastomers, and the like. The composite materials may include, for example, resin impregnated graphite or aramid fibers (e.g., liquid crystal polymers such as Kevlar®), or NiTi dispersed in polyethylene terephthalate. The composite materials may be tailored to define a flexibility gradient, for example, by varying the type and/or amount of filler material therein, which may be controlled or metered during manufacture thereof. Such composite material, thus, can provide the flexible member 14 with a flexibility gradient.

Again, the selected second material has an elasticity different than, either greater or lower than, the first material to provide the flexible member 14 with a variable flexibility. Also, additional materials (third, fourth, fifth materials) with elasticities different than the first and second materials or the same as one of the first and second materials can be used. Determining the elasticity (or moduli of elasticity) of materials is well known in the art. It will be recognized that various other materials suitable for implantation of the flexible member 22 within the human body and for providing stabilization of the spine while maintaining flexibility may be used.

The connecting member 22 generally includes a flexible structure made from materials such as NiTiNOL, a stainless steel coiled wire, or a polymer-based material like polyethylene-terephthalate. Alternatively, the connecting member 22 can be a rigid structure or a combination of a rigid and flexible structure for connection to anchors 16. It will be recognized that various other materials suitable for implantation of the connecting member 22 within the human body and for providing stabilization of the spine while maintaining flexibility may be used.

Referring now to FIGS. 14A-14C, an alternative embodiment of dynamic stabilization system or implant 12 is shown including flexible member 14 of FIG. 1B positioned between anchor members 16. In this embodiment, the connecting members 22 include flanges 52 provided with outwardly projecting annular hubs 53 and a securing element in the form of a setscrew 54. The setscrew 54 is seated within a threaded aperture 56 on the hub 53 to secure the flange 52 and hub 53 arrangement to shank 58 of the system 12 and against the flexible member 14. The system 12 can be assembled pre- or intra-operatively. Once assembled, the system 12 is positioned in the top loading anchor members 16 and secured thereto by the threadable cap members 26, as shown in FIG. 14B, resulting in the arrangement and installation of the flexible member 14. A cross-sectional view of the system 12 and associated anchor members 16 of FIGS. 14A and 14B is shown in FIG. 14C.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and/or method, and illustrative examples shown and described. Accordingly, departures may be made from such details without departing from the scope of applicant's general inventive concept.

What is claimed is:

1. A flexible member for use in stabilizing a spine comprising:
    a polymeric body including opposing first and second ends having an intermediate portion extending therebetween, with each opposing end configured for cooperation with an anchor member, the polymeric body including at least one first portion comprising a first polymeric material having a first elasticity and at least one second portion comprising a second polymeric material having a second elasticity greater than the first elasticity to provide the flexible member with a variable flexibility;
    wherein the first and second portions both extend radially out to a lateral outer edge of the polymeric body;
    wherein the polymeric body includes a lumen extending lengthwise therethrough; wherein the first and second portions both extend radially inward to a surface of the lumen, such that each of the first and second portions defines at least a portion of the surface;
    wherein the at least one first portion comprises a plurality of first portions comprising the first material having the first elasticity and the at least one second portion comprises a plurality of second portions comprising the second material having the second elasticity, and
    wherein the body includes a lengthwise central axis, the plurality of first and second portions extending along the length of the body and being alternately situated about the axis thereof.

2. The flexible member of claim 1 wherein the first material comprises a different polymer than the second material.

3. The flexible member of claim 1 wherein the plurality of first and second portions are alternately situated symmetrically about the axis thereof.

4. The flexible member of claim 1 wherein the elasticity of each of the plurality of first and second portions is different from the other.

5. The flexible member of claim 1 wherein the plurality of first portions define two first portions and the plurality of second portions define two second portions, each of the two first portions and each of the two second portions are situated on opposite sides of the lengthwise central axis from one another, with the elasticity of the two first portions being the same and the elasticity of the two second portions being the same.

6. The flexible member of claim 1 wherein the body defines a cylinder.

7. A flexible member for use in stabilizing a spine comprising:
    a polymeric body including a first end, a second end and a longitudinal axis extending through the polymeric body from the first end to the second end;
    the polymeric body including first and second regions of a first material and first and second regions of a second material, the first material having a first elasticity and the second material having a second elasticity different from the first elasticity;
    wherein each of the first and second regions of the first material extend from the first end to the second end of the polymeric body;
    wherein each of the first and second regions of the second material extend from the first end to the second end of the polymeric body;
    wherein the first and second regions of the first material and the first and second regions of the second material all extend radially out to a lateral outer edge of the polymeric body;
    wherein the polymeric body includes a lumen extending longitudinally therethrough;
    wherein each of the first and second regions of the first material and the first and second regions of the second material extends radially inward to define a surface of the lumen; and
    wherein the first and second regions of the first material are alternately situated about the longitudinal axis with the first and second regions of the second material.

8. The flexible member of claim 7, wherein the polymeric body has a cylindrical shape having a circumference, wherein the first and second regions of the first material span a portion of the circumference of polymeric body and the first and second regions of the second material span a portion of the circumference of the polymeric body.

9. The flexible member of claim 7, wherein the polymeric body has a first bending flexibility in a first plane of bending parallel to the longitudinal axis, and the polymeric body has a second bending flexibility in a second plane of bending parallel to the longitudinal axis, the first bending flexibility being different from the second bending flexibility.

10. A flexible member for use in stabilizing a spine comprising:
   a polymeric body including a first end, a second end and a longitudinal axis extending through the polymeric body from the first end to the second end;
   the polymeric body including first and second regions of a first material and first and second regions of a second material, the first material having a first elasticity and the second material having a second elasticity different from the first elasticity;
   wherein each of the first and second regions of the first material extend from the first end to the second end of the polymeric body;
   wherein each of the first and second regions of the second material extend from the first end to the second end of the polymeric body;
   wherein the first and second regions of the first material and the first and second regions of the second material all extend radially out to a lateral outer edge of the polymeric body;
   wherein the polymeric body includes a lumen extending longitudinally therethrough;
   wherein each of the first and second regions of the first material and the first and second regions of the second material extends radially inward to define a surface of the lumen; and
   wherein each of the first and second regions of the first material is wedged shaped, and each of the first and second regions of the second material is wedged shaped.

11. The flexible member of claim 10, wherein the polymeric body has a first bending flexibility in a first plane of bending parallel to the longitudinal axis, and the polymeric body has a second bending flexibility in a second plane of bending parallel to the longitudinal axis, the first bending flexibility being different from the second bending flexibility.

12. The flexible member of claim 10, wherein the polymeric body has a cylindrical shape having a circumference, wherein the first and second regions of the first material span a portion of the circumference of polymeric body and the first and second regions of the second material span a portion of the circumference of the polymeric body.

* * * * *